United States Patent
Borza

[19]

[11] Patent Number: 6,058,330
[45] Date of Patent: May 2, 2000

[54] TRANSCUTANEOUS ENERGY TRANSFER DEVICE

[75] Inventor: Michael A. Borza, Ottawa, Canada

[73] Assignee: DEW Engineering and Development Limited, Ottawa, Canada

[21] Appl. No.: 09/035,844

[22] Filed: Mar. 6, 1998

[51] Int. Cl.[7] .................................................. A61N 1/08
[52] U.S. Cl. ............................................. 607/61; 607/60
[58] Field of Search ............................... 607/61, 33, 60; 600/16–18

[56] References Cited

U.S. PATENT DOCUMENTS

| | | | |
|---|---|---|---|
| 4,044,775 | 8/1977 | McNichols | 607/61 |
| 4,082,097 | 4/1978 | Mann et al. | 607/33 |
| 4,187,854 | 2/1980 | Hepp et al. | 607/33 |
| 4,441,210 | 4/1984 | Hochmair et al. | 607/61 |
| 4,665,896 | 5/1987 | LaForge et al. | 128/1 D |
| 4,697,183 | 9/1987 | Jenning et al. | 340/870.25 |
| 4,924,171 | 5/1990 | Baba et al. | 323/347 |
| 5,350,413 | 9/1994 | Miller | 607/61 |
| 5,450,076 | 9/1995 | Donig et al. | 340/870.39 |
| 5,495,241 | 2/1996 | Donig et al. | 340/870.39 |
| 5,630,836 | 5/1997 | Prem et al. | 607/61 |
| 5,713,939 | 2/1998 | Nedungadi et al. | 607/33 |
| 5,713,954 | 2/1998 | Rosenberg et al. | 623/3 |
| 5,741,316 | 4/1998 | Chen et al. | 607/61 |
| 5,755,748 | 5/1998 | Borza | 607/61 |

*Primary Examiner*—Kennedy J. Schaetzle
*Attorney, Agent, or Firm*—Neil Teitelbaum & Associates

[57] ABSTRACT

In the design of transcutaneous energy transfer devices, variation in spacing between coils results in energy transfer efficiency changes. These changes may have significant effect on a system. It is proposed to provide a plurality of implanted coils for receiving energy simultaneously. Preferably, a plurality of coil pairs is used for transferring energy simultaneously. Also, a feedback system for use in a multiple coil system is disclosed.

23 Claims, 7 Drawing Sheets

TRANSCUTANEOUS ENERGY TRANSFER DEVICE

Applicant inventor is the inventor of Transcutaneous Energy Transfer Device, disclosed in related U.S. patent application Ser. No. 08/685,813 filed on Jul. $24^{th}$, 1996, now U.S. Pat. No. 5,755,748.

FIELD OF THE INVENTION

This invention relates to the field of medical devices. In particular, the present invention relates to transcutaneous energy transfer (TET) devices.

BACKGROUND OF THE INVENTION

A TET device is a device for providing electrical power to an implanted mechanical or electrical medical device, such as a bone growth stimulator, muscle stimulator, prosthetic heart or a ventricular assist device, without having to breach the skin to lead conducting wires therethrough.

In U.S. Pat. No. 5,350,413 John Miller discloses a TET device with a high-energy transfer efficiency. Such a device allows for efficient transfer of energy between two coils having fixed spacing. Unfortunately, as one coil is located within a body and another coil is located outside the body, maintaining coil separation at a constant distance is difficult. Changes in coil spacing result in variation of the induced voltage and, as the distance increases, the power transfer efficiency drops off rapidly.

In an article entitled "Development of an Autotuned Transcutaneous Energy Transfer System," John Miller, G. Belanger, and T. Mussivand suggest an autotuning circuit to overcome this problem. The autotuning circuit compares various voltages and currents present within a driving circuit external to the body to determine a tuning requirement. Such tuning enables the tuning of energy transfer where the coil spacing varies.

It has been found that the autotuning function disclosed addresses the problem of power coupling efficiency, but fails to address a further problem of internal voltage control. In driving implanted medical devices, energy coupling efficiency and voltage control are separate but related issues to address. Better coupling efficiency results in lower operating cost and improved battery life. Voltage control results in improved device operation and increased safety. In fact, some devices will fail from excessive applied voltage.

Further, it has been found that efficiency is affected by several factors some of which include power coupling related factors such as spacing and load related factors such as medical device load requirements or faults. Unfortunately, autotuning does not address the issue of providing additional energy when required by a medical device.

It has also been found, that prolonged exposure to electromagnetic fields results in damage to human skin. Resulting damage is not believed to be linearly related to the electromagnetic field strength and exposure time. It is believed that high-energy electromagnetic fields above a certain threshold damage human skin and adjacent tissue significantly more rapidly than low energy electromagnetic fields. Since a TET device provides energy to an implanted system and some of these implanted systems require significant power, the damage to tissue such as human skin is a significant drawback to extended use of TET devices. Reducing the electromagnetic field strength and/or reducing exposure time increases tissue longevity.

Two common approaches are known for addressing the problem of tissue damage. The first, skin grafting, is a surgical technique wherein dead tissue is replaced with healthy tissue from another area of a patient's body. Surgical techniques of this type are generally, not desirable. The second technique involves the design and implantation of lower power devices. Unfortunately, a device such as a heart pump requires significant power even when efficiently implemented.

It would be advantageous to provide a TET system that was less prone that the prior art to the problems of tissue damage.

In U.S. Pat. No. 5,350,413, John Miller further discloses an IR telemetry module for providing bidirectional communications. It is known that infra red telemetry is affected by skin pigmentation. As a transceiver disclosed by John Miller is implanted beneath a layer of skin, such considerations are important. It has been found that highly pigmented skin attenuates IR signals and renders a system as disclosed by John Miller substantially unworkable. Further, dirt and other obstructions like clothing or casings affect IR telemetry and can render it inoperable. For a television remote control, this is an acceptable limitation; for medical devices required by an individual, an inoperable TET is unacceptable.

Limitations are inherent in an IR telemetry link. IR is an optical communications means requiring an optical path between transmitter and receiver. Absent fibre or waveguides, IR telemetry is highly directional and limits a system to a single transmitter operating at a time in a direction. The directional nature of IR telemetry requires substantial alignment for optical communication.

Until recently, IR telemetry has been limited to low frequency communications. At low frequencies, it is difficult to multiplex channels, as a serial link requires higher frequencies than a true multi-channel implementation. Unfortunately, as noted above, IR telemetry is not suited to true multi-channel communications. The advent of high speed IR circuits may allow for channel multiplexing using a known technique such as time division multiplexing (TDM); however, this does not overcome previously mentioned shortcomings of IR.

OBJECT OF THE INVENTION

Thus in an attempt to overcome these and other limitations of the prior art it is an object of the present invention to provide a TET having multiple coils for implanting at multiple locations within a patient. Each coil receives a portion of transmitted energy and thereby results in exposure of tissue at each location to electromagnetic fields of lower intensity than result from use of a single pair of coils.

SUMMARY OF THE INVENTION

In a first broad aspect, the invention seeks to provide for a transcutaneous energy transfer device for coupling with a plurality of second coils. The device includes a plurality of first coils, each first coil for performing at least one of transmitting power to and receiving power from a coil from the plurality of second coils; and, a circuit, coupled to each coil from the plurality of coils for performing one of providing power to each coil of the plurality of first coils, the power provided for transmission therefrom, and receiving and combining power from each coil of the plurality of first coils. In an embodiment, the device also includes a plurality of second coils, each coil for transmitting power to a first coil; and a second circuit, coupled to each of the second coils for providing power to each of the second coils, the power provided for transmission from the second coils.

In accordance with the invention there is provided a transcutaneous energy transfer device for coupling with a second coil. The device includes a plurality of first coils, each first coil for performing at least one of transmitting power to and receiving power from the second coil; and a circuit, coupled to each coil from the plurality of coils for performing one of providing power to each coil of the plurality of first coils, the power provided for transmission therefrom, and receiving and combining power from each coil of the plurality of first coils. In an embodiment the plurality of first coils are for receiving power; wherein the circuit is for receiving power from each coil of the plurality of first coils and for combining power from each coil of the plurality of first coils; and, wherein the plurality of first coils are for implanting within a person. In another embodiment the device also includes a plurality of first coils, each first coil for implantation beneath the skin of a patient, the coils for receiving energy in the form of electromagnetic energy transmitted from outside the patient; a plurality of second coils for transmitting power received by the second coils in the form of electromagnetic radiation; a driver circuit for providing power to the second coils; and a circuit for combining the received energy received by the first coils and for providing power to an implanted device.

In accordance with another aspect of the invention, there is provided a method of providing power from an external circuit having a plurality of primary coils to an implanted circuit having a plurality of implanted secondary coils. The method comprises the steps of:

determining an amount of power to provide to the implanted circuit;

dividing the amount of power into a number of portions;

supplying sufficient power to each of a number of the primary coils to result in reception of a portion of the power at each of a number of the implanted secondary coils, the portions received at each of the implanted secondary coils forming the determined amount of power when combined.

In accordance with another embodiment of the invention, there is provided a transcutaneous energy transfer device. The device comprises a primary circuit comprising a plurality of primary coils coupled to at least a primary coil driver, a primary RF transceiver coupled to a plurality of the primary coils for transmitting and receiving RF signals, and primary signal filtering and extraction means for extracting information from the RF signal received by the primary RF transceiver; and a secondary circuit comprising a plurality of secondary coils, a secondary RF transceiver coupled to a plurality of the secondary coils, and secondary signal filtering and extraction means for extracting information from the RF signal received by the secondary RF transceiver.

BRIEF DESCRIPTION OF THE DRAWINGS

Exemplary embodiments of the invention, will now be described in conjunction with th e following drawings, in which.

DETAILED DESCRIPTION OF THE INVENTION

Figure 1:
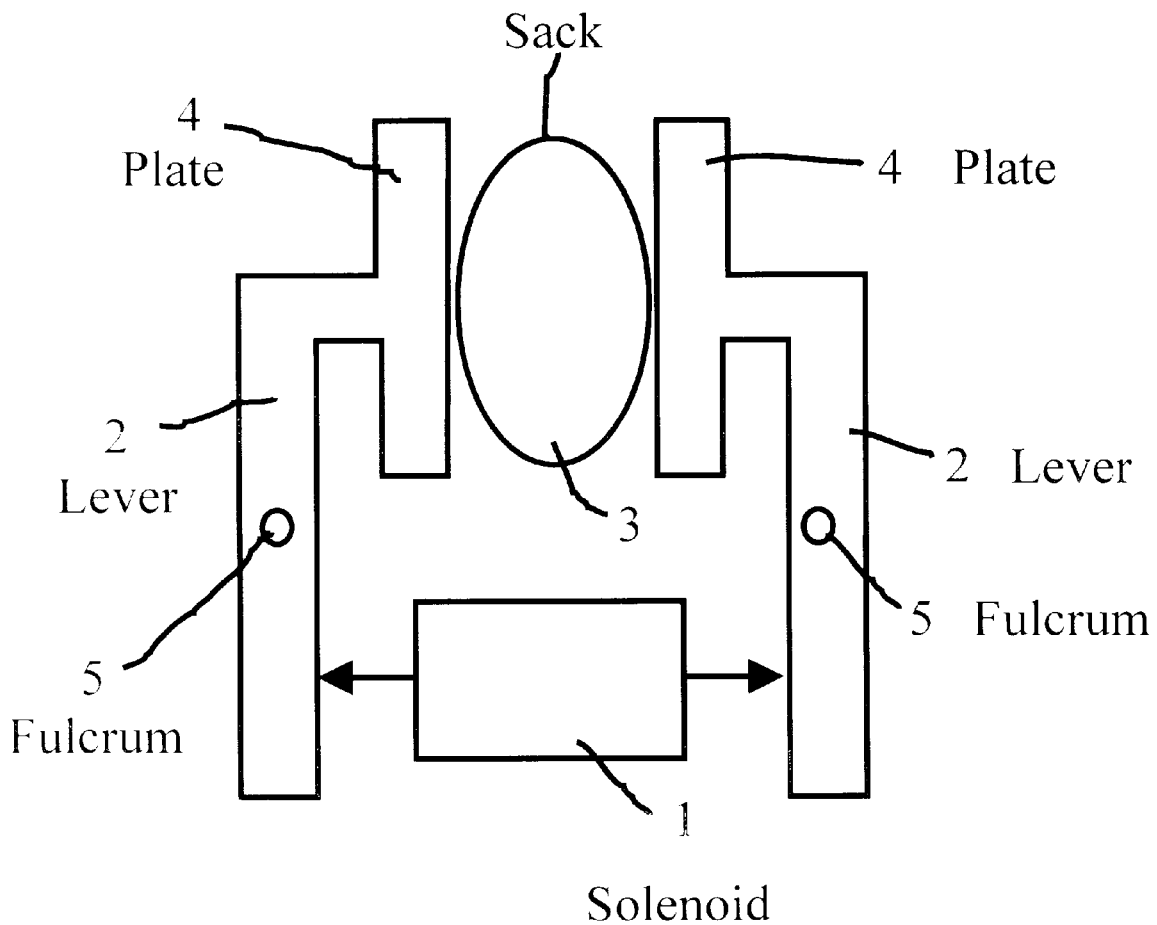
FIG. 1 is a simplified diagram of a Baxter Pharmaceutical® Pump.

Referring to FIG. 1, a Baxter Pharmaceutical® Pump is shown. The heart assist device operates to pump blood within a body. A solenoid 1 separates two levers 2. At an opposite end, the levers 2 are connected to compression means in the form of plates 4 that push against a sack 3. The compression of the sack 3 results in a pumping action. A fulcrum 5 is shown in order to clarify the motion of the levers 2.

This pumping action requires that the solenoid 1 receive adequate power. The solenoid 1 is provided power in an alternating fashion. Power is only provided while the solenoid 1 exerts force on the levers 2. Alternatively, power is provided all the time and the device converts the power signal into an alternating power signal. The conversion can be accomplished using energy storage and discharge means. Once the sack 3 is compressed, the solenoid must be turned off to allow the sack 3 to fill with fluid. Further, the solenoid 1 draws little power except when compressing the sack 3. Even during compression, power requirements vary throughout a stroke. The operation is well documented in the prior art.

The operation of the pump and similar devices draws energy inconsistently. As the load increases, voltage in the power supply is affected as is drive current. Increasing power supply voltage may result in voltage spikes when the load is removed. These power spikes are capable of damaging some devices. An approach to preventing this problem is to include voltage regulation means within each device to protect against power surges and voltage spikes. Prior art advances have addressed issues of power delivery and circuit tuning. Methods are known wherein voltage is regulated through a feed back loop or through autotuning.

Figure 2:
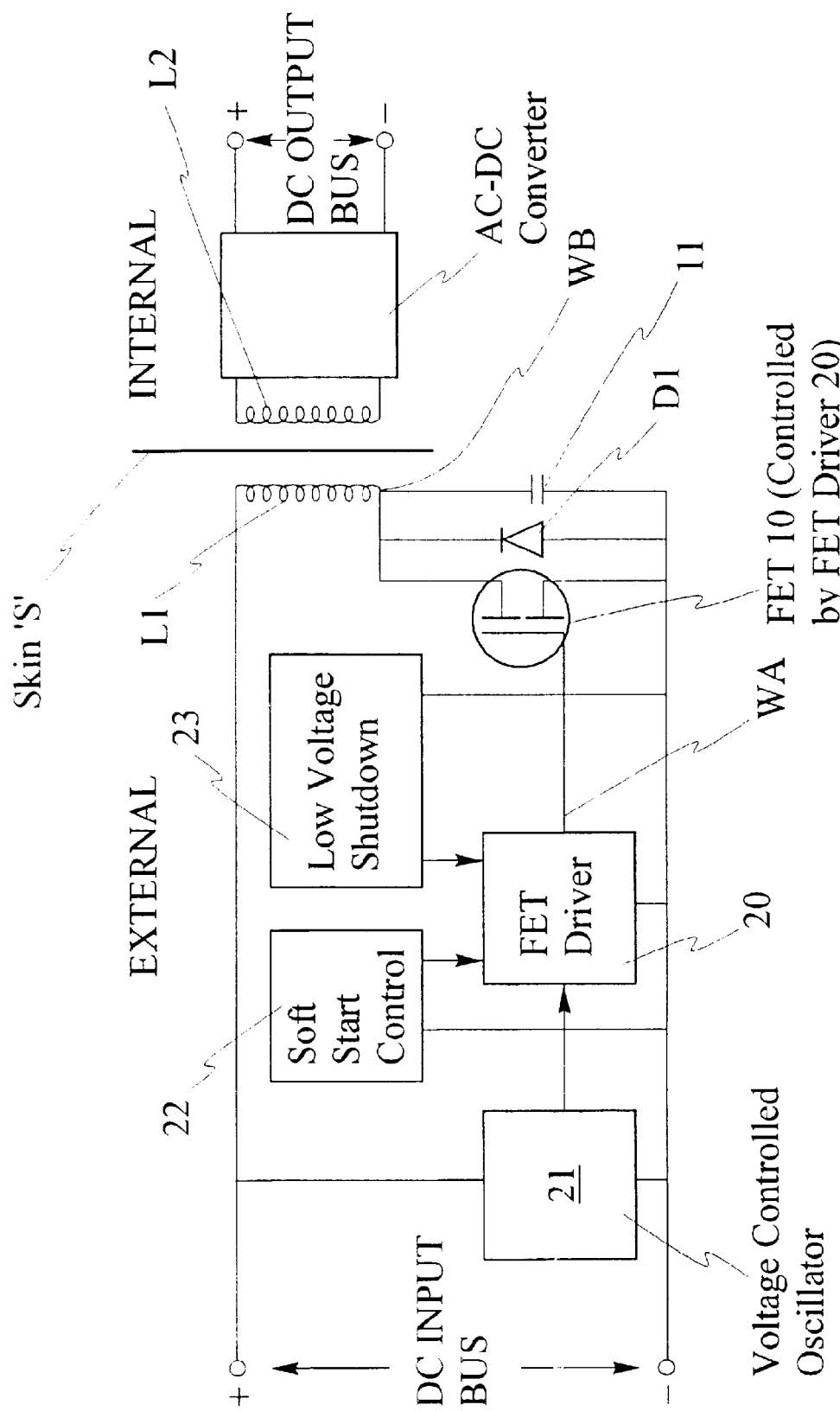
FIG. 2 is a circuit diagram of a TET according to the prior art.

Referring to FIG. 2, a TET device, known in the prior art, is shown. The device comprises a transformer designed to induce AC current in a subcutaneous winding for transformation to DC voltage for use in powering a medical device. Alternatively, the induced AC current is used to power a medical device. AC current is induced in L2, the secondary winding which may be, for instance, a torus core, wound with Litzendraht wire implanted just beneath the surface of the skin S with electrical leads connected to a medical device. A similar primary winding L1 is located in alignment with the secondary winding, on the skin surface and exterior thereto.

Primary winding L1 is connected to a capacitor 11 that is connected to the negative of a DC input bus. As indicated in FIG. 2, winding L1 is also connected to a field effect transistor (FET) 10 controlled by FET driver 20. FET driver 20 receives inputs from voltage-controlled oscillator 21, soft start control 22 and low voltage shutdown 23 to produce an alternating or pulsing waveform.

Power transfer may be considered to take place in two phases, a storage phase and a resonant phase. During the storage phase, energy is stored in the primary coil using a FET to switch the coil directly across the DC input supply.

The FET is selected for its very low "on" resistance to minimise conduction losses.

As shown in FIG. 2, the coil L2 is implanted under the skin S. The remainder of the circuit remains external to the skin. Voltage is induced in the coil L2 from the coil L1, said coil and driver circuitry therefor remaining external to the skin S. Skin is capable of suffering damage from exposure to electrical fields for prolonged periods of time. Therefore, in designing TET devices, it is very useful to limit the electrical field necessary to induce sufficient voltage to provide necessary power.

Unfortunately, prior art circuits and methods do not address the significant problem of tissue damage. As discussed above, tissue damage results from prolonged exposure to electromagnetic fields. It is believed that reducing the field strength below a threshold field strength greatly increases tissue life. A method and device are presented herein for reducing the field strength across a patient's skin.

Figure 3:
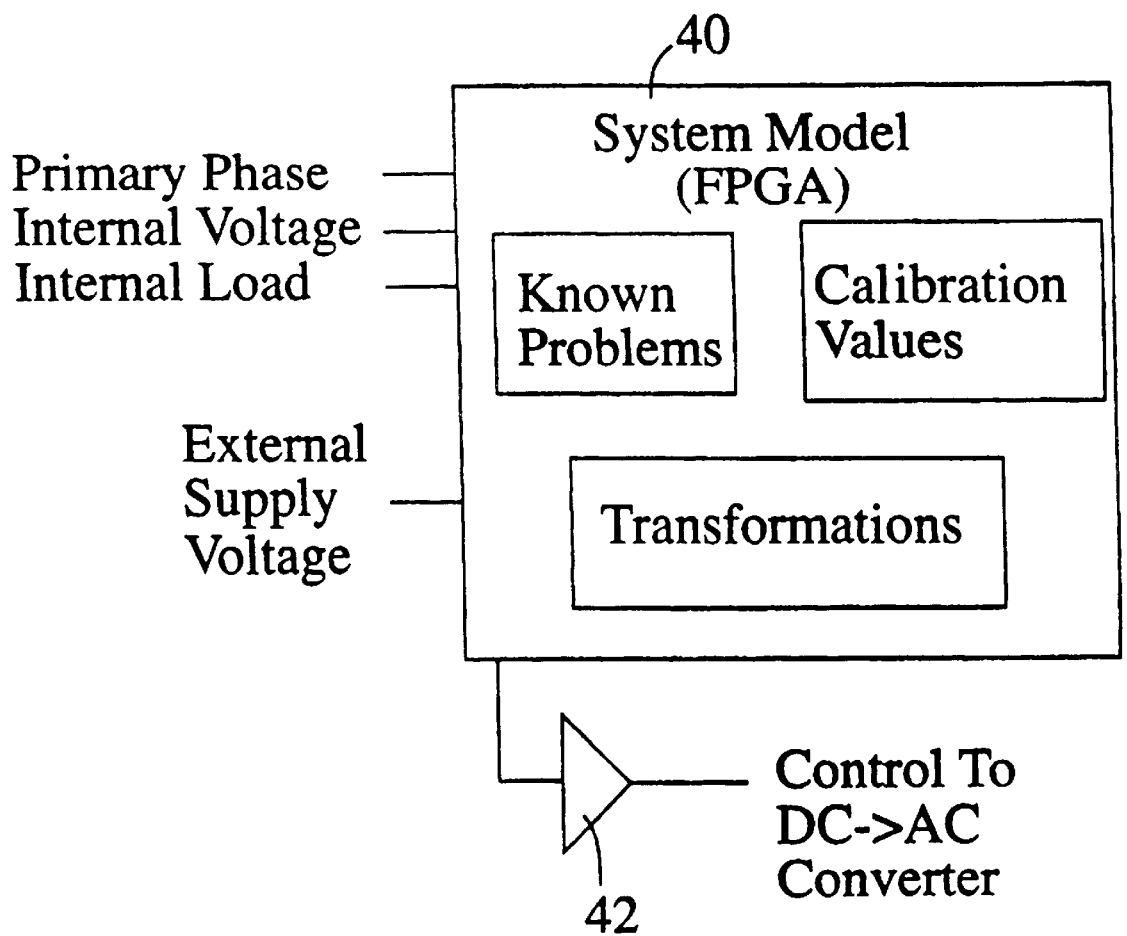
FIG. 3 is a block diagram of an integrated voltage control and autotuning circuit implemented in an FPGA.

Referring to FIG. 3, an integrated voltage control autotuning circuit implemented in an FPGA is shown. Measurements of internal voltage and internal load are supplied to the control circuit via a telemetry link with a subcutaneous circuit (shown in FIG. 4). Such telemetry links are known using IR transmission and RF transmission. Based on the supplied values, the control circuit assesses the voltage control needs and the coupling efficiency in order to maintain appropriate levels of energy for the medical device. The FPGA controls the DC to AC converter, in the form of a plurality of FET drivers 20 and a power control circuit 43 (shown in FIG. 4), based on these values and based on system knowledge or calibration values. The FET drivers 20 are also used to control frequency and duty cycle. The circuit within the FPGA may incorporate other aspects of the TET circuitry.

Since a TET system must operate over various conditions, it is preferable that a control circuit has information relating to current conditions in order to set the correct operating point. In order to effectively autotune the TET and control voltage one of two methods is required. A first method comprises feedback from the coils L2. This feedback along with a circuit designed to correct voltage and to tune the circuit based on the feedback allow for improved operation of the TET. Alternatively, a sufficiently large number of coils operating efficiently within narrow ranges are employed and, even absent feedback, provide a secure and efficient coupling to a plurality of internal coils. Of course, feedback also provides valuable information relating to the internal device, patient health, TET failure, battery failure when a battery is used, and so forth.

When feedback of measured values is used, the programmable circuit responds to the measured values. When two values are measured in the form of load current and voltage, the measured values are low, normal, or high resulting in 9 possible combinations for each coil L2 from the plurality of coils L2. In this embodiment, phase is corrected using phase correction circuitry independent of the programmable circuit. For each of the 9 possible combinations the programmable circuit responds. The response may, for example, drift values toward an acceptable range. When measured load of a particular coil L2 increases, induced current is increased to maintain induced voltage substantially constant. When measured voltage increases, induced voltage is lowered to maintain induced voltage substantially constant. This effectively improves operation of the TET and prevents surges that can damage implanted devices. Further, since a plurality of coils are used to transmit and receive power across the skin, the skin at each coil location receives a fraction of the electromagnetic field strength required when using a single pair of coils, as taught in the prior art.

Alternatively, a single load measurement is used and the coils L2 are controlled in accordance therewith. In an embodiment, for example, each coil receives an equal fraction of the transmitted energy. In another embodiment, coils are driven as determined through calibration. According to yet another embodiment, each coil provides some feedback relating to coupling efficiency in order to maximise overall energy usage while maintaining electromagnetic radiation across the skin below the predetermined threshold.

Of course, phase correction circuitry may be implemented in association with the feedback information. Also, other corrective action may be implemented in order to maintain a desired coupling between external coils and implanted coils during operation of the TET device.

Different embodiments of control systems for maintaining sufficient power levels in the implanted circuit include the following features: a feedback loop for responding to current and past measured values; calibration of the circuitry to function with a specific implanted device; and/or calibration undertaken during an initial period of use, and an ongoing estimation of tissue damage due to electromagnetic field strengths and overall exposure times. A calibrated programmable circuit allows for corrective actions in anticipation of change. The system, for example, includes storage means for storing past sequences of measured values that were controlled inadequately. When these patterns occur, the programmable circuit responds differently than in previous attempts (within acceptable parameters) to better address the measured values. Estimation of tissue damage permits control of multiple external coils in an attempt to minimise overall tissue damage. For example, during a period of high demand, most but not all coils are driven to a higher than acceptable level. Once demand is reduced, those coils which were not driven above acceptable levels, are provided with a greater proportion of the energy to provide time for the tissue exposed to higher than acceptable levels of energy to recover from the exposure. Also, when coupling efficiency is reduced in a particular coil, decisions regarding which coil(s) will transfer that energy are related to the estimates of potential tissue damage.

Low internal voltage is caused by poor coupling or by high internal load. Providing both voltage and load from the internal coil to the external control circuit thereby allows for assessment of cause and appropriate control response. Of course, other feedback is also useful. For example, feedback relating to measured tissue damage, device operation, battery power level when a battery is used, coupling efficiencies, and so forth are useful with a multiple implanted coil implementation of a TET device.

Further, the use of multiple implanted coils has other advantages. Increased reliability occurs when each coil is capable of providing a large fraction of the necessary power or when there is a large number of coils. An external circuit failure has limited effect when many external circuits provide power to the implanted device. This is even more so when feedback indicates such a failure allowing for corrective action. Movement or misalignment of an energy source results in an indication of misalignment. This indication results in reduced power to that misaligned coil pair and increased power to other, better aligned pairs.

Figure 4:
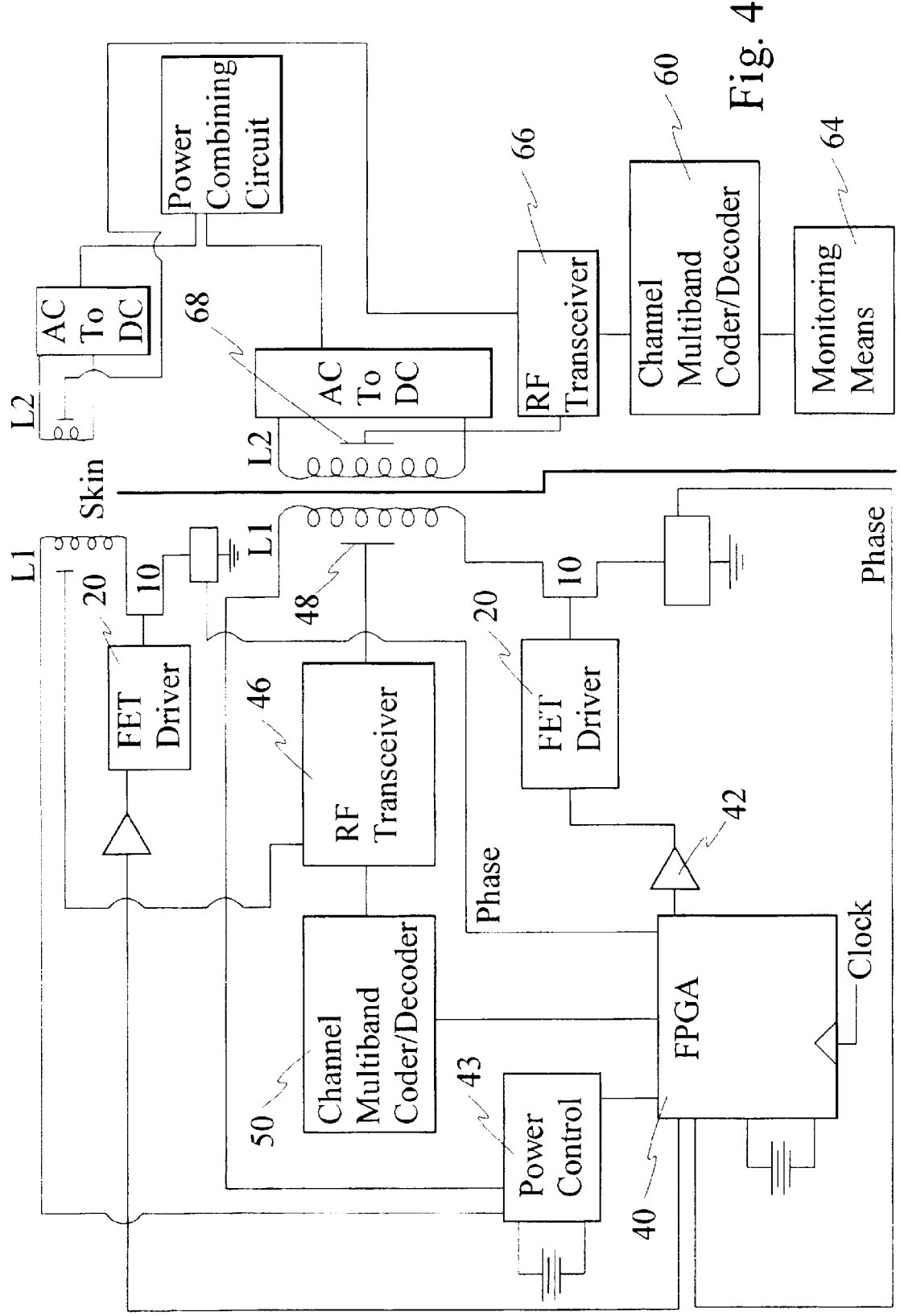
FIG. 4 is a partial circuit diagram of an RF telemetry system according to the present invention.

Turning to FIG. 4, a block diagram of a TET system according to an embodiment of the present invention and incorporating the programmable circuit of FIG. 3 is shown.

The programmable circuit 40 in the form of an FPGA drives a plurality of FET drivers 20 and a power control circuits 43. The FET drivers 20 switch transistors 10 to drive the primary coils L1 in an alternating fashion. The power control circuits 43 control current and voltage provided to the coils L1 when switch transistors 10 are switched "on." The programmable circuit 40 receives inputs comprising timing in the form of a clock, power in the form of a voltage input, and monitored values received from at least a subcutaneous circuit via a telemetry link. The control functions within the programmable circuit 40 are dependent upon the received signals. Though a telemetry link in the form of an RF telemetry link is shown in FIG. 4, with the programmable circuit 40 any telemetry link providing a capability to transmit or receive all necessary monitored information will work. It is, however, preferable to use a true multi-channel communications means according to the present invention.

The RF transceiver 46 receives a signal via an antenna means 48 in the form of an RF antenna tuned to a predetermined frequency. Alternatively, the antenna means forms an integral part of the primary coil L1 (shown in FIG. 5). The received RF signal (at the RF transceiver 46) is filtered to reduce noise and remove unnecessary signals. Alternatively, this step is performed in the channel multi-band encoder/decoder 50. It is then decoded into individual channels or individual monitored values.

The channel structure of the information incorporates a channel for control information and a plurality of channels for monitored information. Control information is transmitted from the external circuit to the subcutaneous circuit. The subcutaneous circuit transmits diagnostic indicators in the form of bearing condition, blood sack shape, and device failure to the external circuit. Alternatively, the internal circuit sends control signals as well as diagnostic signals to the external circuit. In order to send a plurality of monitored values via a single channel, a method such as time division multiplexing (TDM) is employed. Using TDM, each value is assigned a time slot that repeats every frame. Within each frame a plurality of time slots each contains a value indicative of a measured or monitored characteristic. In each frame, the order of the plurality of channels is the same and, therefore, a value for each monitored characteristic is obtained by sampling the channel for that characteristic. Alternatively, when implanted coils are located a sufficient distance one from another, each coil transmits a single channel of information. Of course, duplication of transmitted information by transmitting same information from several implanted coils improves system robustness. Alternatively, a separate transceiver is used for transmitting information.

An example will demonstrate TDM. When 8 channels are within each frame, any value can be sampled based on the frame's frequency. Commonly, a frame pulse or a frame indicator signal are incorporated in order to align a transmitter and a receiver. From a frame's beginning a first channel value is sampled. From a frame's beginning+Δt(n/8 of a frame's period) an nth channel is sampled. In this way, a plurality of channels are transmitted across a single physical channel using serial communications. It is preferable to maintain at least some channels for security information to ensure that the telemetry link is between predetermined circuits. This is to minimise effects of stray signals.

A subcutaneous circuit comprises secondary coils L2 similar to the primary coils L1. An antenna 68 is disposed near the secondary coils L2 and in co-operation with an RF transceiver 66 sends monitored signals to the external circuit. Alternatively, monitored signals and control signals are transmitted. Alternatively, the secondary coils L2 also act as antennas. As with the external received and transmitted signals, noise is present in the subcutaneous received and transmitted signals in the form of white noise and cross talk from the power signal. A channel multi-band encoder/decoder 60 filters the noise and extracts desired signals. The channel multi-band encoder/decoder 60 also encodes monitored values to form appropriate RF signals in order to improve transmission effectiveness. Means such as forward error correction or parity are employed to improve the accuracy of the received and decoded signals.

The cross talk induced in a received signal is significant. A TET transmits energy via a coil pair. The energy transferred is often over 50 watts. The RF telemetry signal required to communicate between subcutaneous and external circuits transmits at a power level of several milliwatts. It is therefore important to shield circuitry (both external and subcutaneous) to ensure that once filtered, cross talk is not reintroduced. In a further embodiment, monitoring characteristics of at least some of the RF signals received, transmitting values in dependence upon the characteristics, and varying the RF signal parameters in the form of strength and frequency are implemented to improve telemetry robustness.

The channel multi-band encoder/decoder 60 receives information to encode for transmission from the monitoring means 64. The monitoring means for voltage and current form part of the AC to DC converter circuit when one exists. Alternatively, separate monitoring means are implemented. Of course, monitoring means are implemented to monitor any characteristic desirable in the subcutaneous circuit and in the implanted medical device.

In association with the improved power coupling control mechanism described herein, the RF telemetry system allows for a sufficient number of characteristics such as phase, voltage, drive current, bearing wear, battery status, and other non-essential characteristics such as blood flow, or muscle contraction. Each said characteristic is monitored internal to a body and transmitted via RF telemetry to an external control and monitoring circuit. Alternatively, external monitoring is also performed to indicate power signal voltage, communications signal strength, etc. and transmit monitored values via RF telemetry to a subcutaneous circuit. The use of RF telemetry, allows for each monitored characteristic to occupy a single channel or alternatively, for multiplexing a plurality of characteristics onto a single channel using a known method such as TDM.

Using RF telemetry, it is preferable to maintain a security ID or another form of transmitter verification to prevent effects of stray signals and to limit circuit response to signals originating from an appropriate transmitter.

Figure 5:
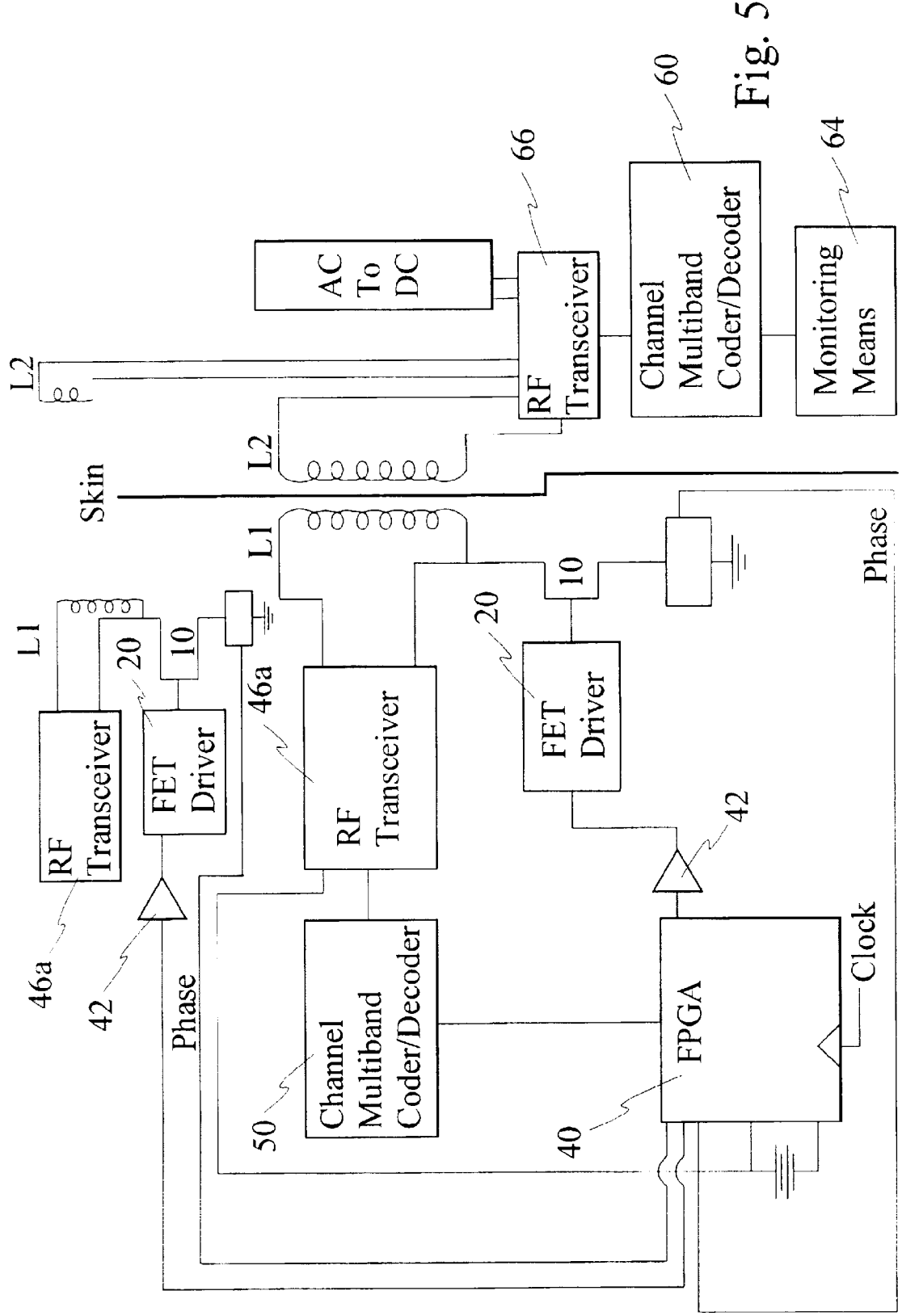
FIG. 5 is a partial circuit diagram of an alternative RF telemetry system according to the present invention.

Referring to FIG. 5, another embodiment wherein same coils act as transceivers of energy and information is shown. Here, a second antenna for transmitting information is not necessary.

Figure 6A:
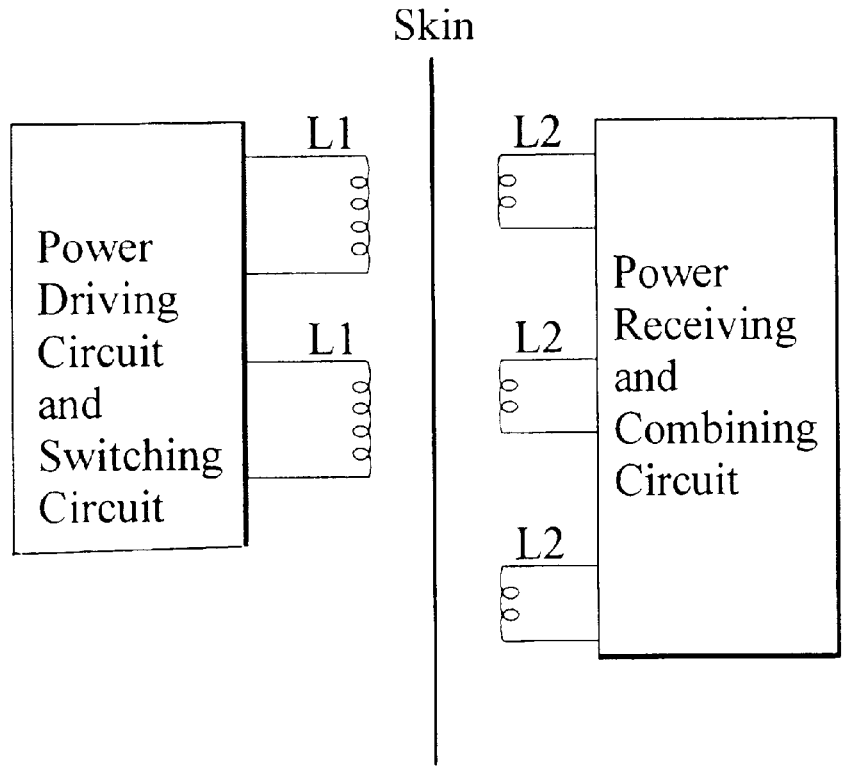
FIG. 6a is a simplified diagram of a plurality of embedded coils according to the invention and associated circuitry.

Referring to FIG. 6a, an embodiment of the invention is shown using fewer external coils than internal coils. When coupling efficiency is of significant concern, energy levels are desired to be low, and the external coil(s) move as is currently the case, it is advantageous to couple a majority of energy from the external coil(s) to the internal coils.

Figure 6B:
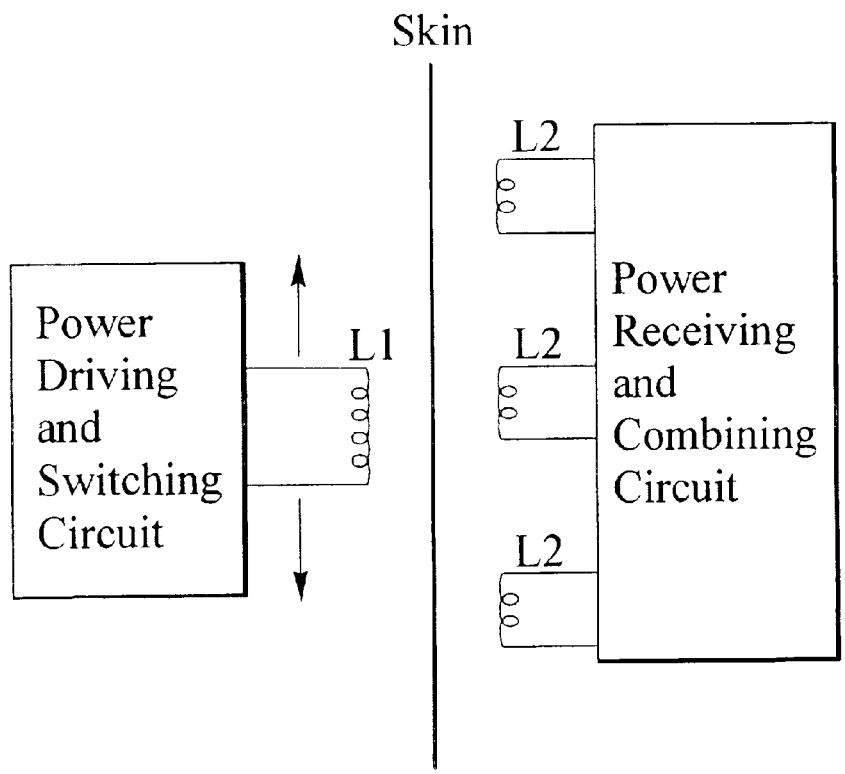
FIG. 6b is a simplified diagram of a plurality of embedded coils according to another embodiment of the invention and associated circuitry.

As shown in FIG. 6b, a single external coil is disposed in close proximity to a patient. Implanted beneath the patient's skin is a plurality of secondary coils. The secondary coils are implanted in a pattern determined based on common types of movement of the external coil. For example, when the external coil is subject to movement in only one direction (Shown with arrows in FIG. 6b), coils are stacked as shown. The result is that movement that would have resulted in a significant loss of coupling efficiency, now results in a coupling with a different secondary coil. Coupling efficiency is maintained. Even during the transition, coupling efficiency is improved because coupling occurs with each of two secondary coils and, thereby, allows for more of the transmitted energy to be received by the implanted coils.

Figure 7:
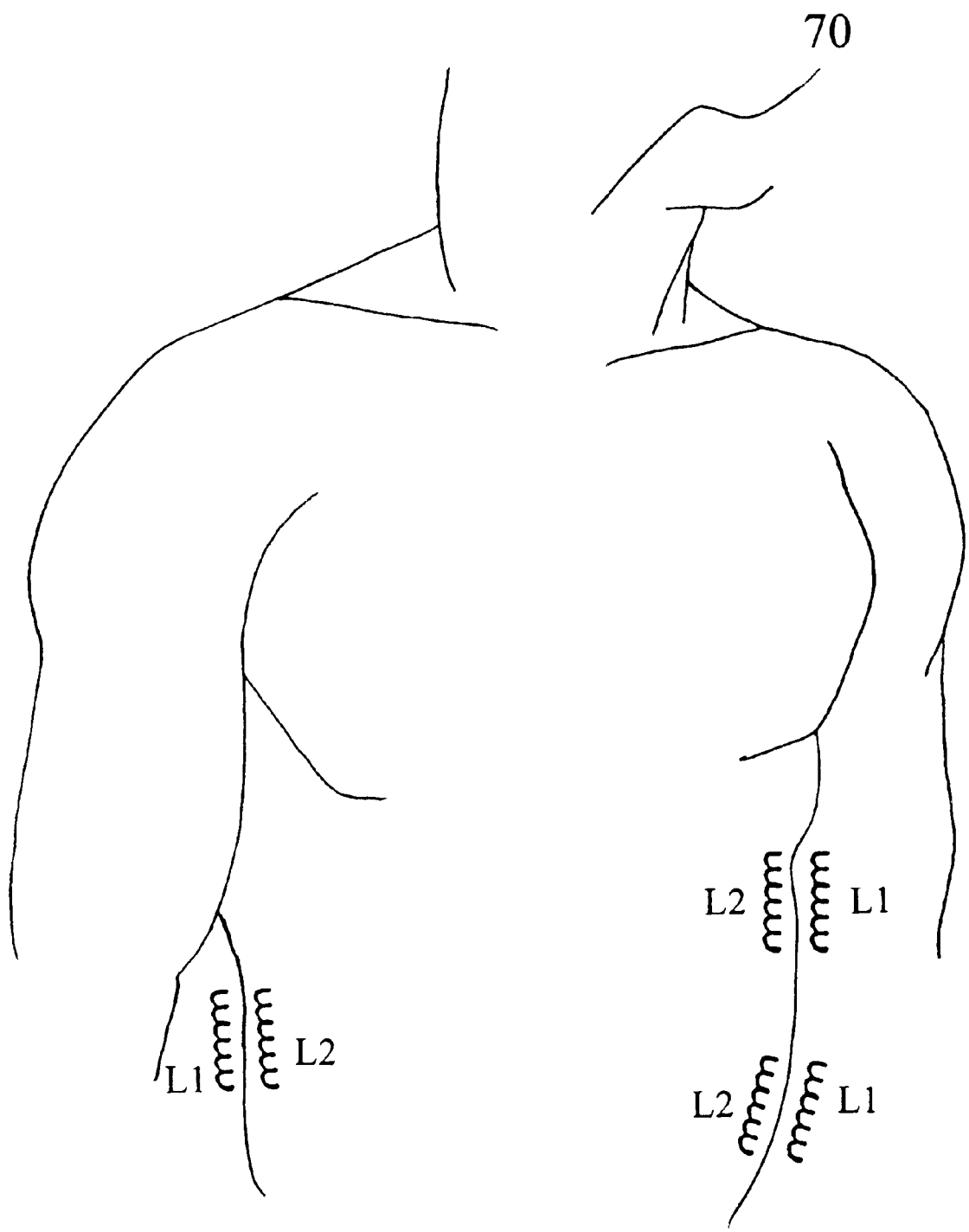
FIG. 7 is a simplified diagram of a transcutaneous energy transfer device according to the invention wherein coils are implanted at many locations within a patient.

The internal coils are connected to a summing circuit where energy received is combined to form a single power signal. With the embodiment of FIG. 6a, further advantages exist in that a same internal coil couples with one external coil or another depending on the direction in which the external circuit has been moved. Obviously, allowing the external circuit to move relative to the internal circuit presents advantages in the form of increased patient comfort Referring to FIG. 7, an embodiment is shown wherein the implanted coils L2 are disposed at many locations within the patient 70. This permits significant flexibility in terms of apparel and also provides for a large amount of circuit redundancy. Redundancy helps improve reliability. Some of the coil pairs L1, L2 shown may be replaced with multiple coil couplings shown in FIG. 6a. Each pair acts to independently transmit energy across tissue. The control circuitry acts to direct appropriate amounts of energy to each coil so as to reduce tissue damage while ensuring adequate energy for implanted device operation. Of course an absence of an external coil is not catastrophic when using a TET system according to the present invention.

According to an embodiment, exposure monitoring is performed for tissue exposed to electromagnetic radiation. The monitoring produces data that is stored as historical exposure data. Coils are provided with power in order to minimise potential damage based on historical exposure data, medical data provided through checkups of exposed regions, and required energy transmission levels. Using such a system, an adaptive approach that is capable of being customised to a particular user is provided wherein medical information provided during check-ups is then used to evaluate the significance of the historical exposure data and therefore allow for reduced overall tissue damage.

Numerous other embodiments may be envisaged without departing from the spirit and scope of the invention.

What I claim is:

1. A transcutaneous energy transfer device comprising:
  a) a plurality of first coils, each first coil for performing at least one of transmitting power and receiving power;
  b) a first circuit, coupled to each coil from the plurality of first coils for performing one of providing power to each coil of the plurality of first coils, the power provided for transmission therefrom, and receiving power from each coil of the plurality of first coils;
  c) a plurality of second coils, each second coil for performing one of transmitting power to and receiving power from a coil of the plurality of first coils;
  d) a second circuit, coupled to each coil of the plurality of second coils for performing one of providing power to each coil of the plurality of second coils, the power provided for transmission therefrom, and receiving and combining power from each coil of the plurality of second coils; and,
  e) a control system for maintaining provision of a sufficient amount of power to the second circuit, wherein a portion of the power is received at each of the plurality of second coils, the portions received at each of the second coils forming approximately the sufficient amount of power when combined, and wherein the power provided to some of the first coils for transmission is varied in order to transmit the sufficient amount of power to the plurality of second coils such that damage to a medium between the plurality of first coils and the plurality of second coils due to induced electromagnetic fields is controlled within predetermined limits.

2. A transcutaneous energy transfer device as defined in claim 1 wherein the plurality of second coils are for receiving power; wherein the second circuit is for receiving power from each coil of the plurality of second coils and for combining power from each coil of the plurality of second coils; and, wherein the second circuit and the plurality of second coils are for implanting within a person.

3. A transcutaneous energy transfer device as defined in claim 2 wherein a first coil and a second coil form a coil pair, and wherein the coils are arranged to form a plurality of coil pairs, the device comprising means for transmitting between a plurality of coil pairs a same RF signal.

4. A transcutaneous energy transfer device as defined in claim 2 comprising means for measuring at least a characteristic of some coils from the plurality of second coils during operation and transmitting an indication of the at least a characteristic.

5. A transcutaneous energy transfer device as defined in claim 1 wherein a first coil and a second coil form a coil pair, and wherein the coils are arranged to form a plurality of coil pairs, wherein the control system comprises:
  means for determining a coupling efficiency between coils of a coil pair and for limiting power provided to each of the second coils in dependence upon the determined coupling efficiency.

6. A transcutaneous energy transfer device as defined in claim 1 wherein a first coil and a second coil form a coil pair, and wherein the coils are arranged to form a plurality of coil pairs, wherein the control system comprises:
  means for providing energy at a predetermined threshold energy level to each of the first coils and wherein a number of first coils is switchably provided with said energy at the predetermined threshold level in dependence upon a determined amount of energy for transmission.

7. A transcutaneous energy transfer device as defined in claim 1 wherein a first coil and a second coil form a coil pair, and wherein the coils are arranged to form a plurality of coil pairs, wherein the external circuit comprises:
  means for determining an amount of energy to transfer and for providing energy to a plurality of external coils such that each coil transmits a portion of the determined amount of energy, the sum of the portions being equal or greater than the determined amount of energy.

8. A transcutaneous energy transfer device as defined in claim 7 wherein the energy provided to a plurality of first coils is provided such that each coil transmits energy below a predetermined threshold energy level.

9. A transcutaneous energy transfer device as defined in claim 7 wherein the control system comprises means for approximating an amount of tissue damage caused by energy transmission from some of the plurality of coils and wherein the energy provided to a plurality of external coils is provided in dependence upon the estimation.

10. A transcutaneous energy transfer device for coupling with at least a first coil comprising:
  a) a plurality of second coils, wherein the plurality of second coils comprises a number of coils different from the number of the at least first coil, each second coil for performing at least one of transmitting power to and receiving power from the at least first coil; and, b) a circuit, coupled to each coil from the plurality of second coils for performing one of providing power to each coil of the plurality of second coils, the power provided for transmission therefrom, and receiving and combining power from each coil of the plurality of second coils.

11. A transcutaneous energy transfer device for coupling with at least a first coil as defined in claim 10 wherein the plurality of second coils are for receiving power; wherein the circuit is for receiving power from each coil of the plurality of second coils and for combining power from each coil of the plurality of second coils; and, wherein the plurality of second coils are for implanting within a person.

12. A transcutaneous energy transfer device for providing electrical power to a medical device implanted beneath the skin of a patient comprising:

a) a plurality of first coils for transmitting power in the form of electromagnetic radiation, wherein the plurality of first coils comprises three or more first coils;

b) a plurality of second coils, each second coil for implantation beneath the skin of the patient beneath different segments of tissue at different locations, the plurality of second coils for receiving energy in the form of electromagnetic energy transmitted from the first coils outside the patient, wherein the plurality of second coils comprises three or more second coils;

c) a first circuit for providing power to the first coils;

d) a second circuit for implantation beneath the skin of the patient, the second circuit for combining the power received by the second coils and for providing power to an implanted device.

13. A transcutaneous energy transfer device as defined in claim 12, wherein the first circuit comprises a control system for maintaining provision of a sufficient amount of power to the medical device, wherein a portion of the power is received at each of the plurality of second coils, the portions received at each of the second coils forming approximately the sufficient amount of power when combined, and wherein the sufficient amount of power received at the plurality of second coils is transmitted between the plurality of first coils and the plurality of second coils such that tissue damage to the patients skin due to induced electromagnetic fields is reduced over damage resulting from transmission of same energy across tissue at a single location.

14. A transcutaneous energy transfer device as defined in claim 12, wherein in use tissue covering a different coil is not substantially damaged by energy provided to another coil of the plurality of second coils, the other coil beneath a different segment of tissue from the different coil.

15. Transcutaneous energy transfer device comprising:

a primary circuit comprising a plurality of primary coils coupled to at least a primary coil driver, a primary RF transceiver coupled to a plurality of the primary coils for transmitting and receiving RF signals, and primary signal filtering and extraction means for extracting information from the RF signal received by the primary RF transceiver; and a secondary circuit comprising a plurality of secondary coils, a secondary RF transceiver coupled to a plurality of the secondary coils, and secondary signal filtering and extraction means for extracting information from the RF signal received by the secondary RF transceiver.

16. The transcutaneous energy transfer device of claim 15 further comprising:

a) means for measuring characteristics of at least a secondary coil from the plurality of secondary coils during operation and transmitting an indication of the characteristics;

b) a voltage control circuit, and c) means for receiving the transmitted indication of the characteristic and providing a control signal in dependence upon the indication to the voltage control circuit, wherein the voltage control circuit is for controlling at least one of voltage and current independently in each of the plurality of primary coils in dependence upon a received control signal.

17. A method of providing power from an external circuit having a control system and a plurality of first coils to an implanted circuit having a plurality of implanted second coils comprising the steps of:

determining an amount of power to be provided to the implanted circuit;

using the control system for dividing the amount of power into a number of portions such that tissue damage to a patients skin due to induced electromagnetic fields is minimized and for determining sufficient power to be provided to each of a number of the first coils to result in reception of a portion of the power at each of a number of the implanted second coils, the portions received at each of the implanted second coils forming approximately the determined amount of power when combined; and, supplying the sufficient power to each of a number of the first coils.

18. A method of providing power from an external circuit to an implanted circuit as defined in claim 17 comprising the step of: combining the energy portions received at each of the implanted second coils.

19. A method of providing power from an external circuit to an implanted circuit as defined in claim 17 comprising the step of: using the control system for determining a coupling efficiency for energy transmitted from some first coils to some second coils.

20. A method of providing power from an external circuit to an implanted circuit as defined in claim 19 comprising the step of: providing additional energy to first coils determined to have efficient coupling with associated second coils.

21. A method of providing power from an external circuit to an implanted circuit as defined in claim 17 comprising the step of: providing a same communication signal from each of a plurality of second coils.

22. A method of providing power from an external circuit to an implanted circuit as defined in claim 17 wherein each portion is substantially identical.

23. A method of providing power from an external circuit to an implanted circuit as defined in claim 17 wherein each portion is a predetermined amount of power and wherein a number of first coils is switchably provided with the portion in dependence upon the determined amount of power.

* * * * *